United States Patent [19]

Paul et al.

[11] Patent Number: 4,933,286
[45] Date of Patent: Jun. 12, 1990

[54] PURIFICATION OF APASE-1$_1$ AND RETRIEVAL OF THE NEMATODE RESISTANCE GENE

[75] Inventors: Elizabeth M. Paul, Leicester, England; Valerie M. Williamson; Jack L. Erion, both of Dublin, Calif.; Candace G. Poutre, San Ramon; Calif.

[73] Assignee: Plant Cell Research Institute, Inc., Dublin, Calif.

[21] Appl. No.: 32,418

[22] Filed: Mar. 30, 1987

[51] Int. Cl.$^5$ ............................................. C12N 9/18
[52] U.S. Cl. .................................... 435/197; 435/815
[58] Field of Search ................ 530/412, 379; 435/196, 435/197; 455/815

[56] References Cited

PUBLICATIONS

Ozutsumi et al., "Immunological Properties of Two Acid Phosphatases from Tomato Fruit", *Agr. Biol. Chem.*, vol. 47 (5) (1983), pp. 1137–1138.
Uehara et al., "Isolation of Violet-Colored Acid Phosphatase from Sweet Potato", *J. Biochem*, vol. 70 (1971), pp. 183–185.
Karger et al., *An Introduction to Separation Science*, John Wiley & Sons, N.Y., (1973), p. 338.
Medina–Filho, Ph.D. Thesis (1980) University of California, Davis.
Forbes et al., *Tomato Genetics Cooperative Reports* (1976) 26:7–8.
Rick et al., *Tomato Genetics Cooperative Reports* (1974) 24:25.
Rick, *Genetic Maps* (1984) 3:474 Cold Spring Harbor Press.
Bennetzen, *Genetic Engineering* (1984) pp. 491–512.
Collins et al., *Proc. Natl. Acad. Sci.* (1984) 81:6812–6816.
Martin et al., *Nucleic Acids Research* (1985) 13:8927–8938.
Poustka et al., *Nature* (1987) 325:353–355.
Poustka et al., *TIC* (1986) pp. 174–179.
Reyes et al, *Genetic Engineering* (1985) pp. 157–173.
Steinmetz et al., *Nature* (1982) 300:35–42.

Primary Examiner—Thomas G. Wiseman
Assistant Examiner—S. Nolan
Attorney, Agent, or Firm—Irell & Manella

[57] ABSTRACT

An isoenzyme from tomato, acid phosphatase-1 isoenzyme (Apase-1$^1$), has ben purified to homogeneity and is subjected to amino acid sequencing and used to prepare anti-Apase-1 antibodies. The amino acid sequence permits design of probes to recover Apase-1$^1$-encoding cDNA; the antibodies are also useful for this purpose. The cDNA is useful to recover the genomic DNA encoding Apase-1$^1$, which can then be used in walking or jumping techniques to recover the genomic DNA which confers nematode resistance, since this DNA resides immediately adjacent to the Apase-1$^1$ gene on chromosome 6 of *Lycopersicon esculentum*.

6 Claims, 3 Drawing Sheets

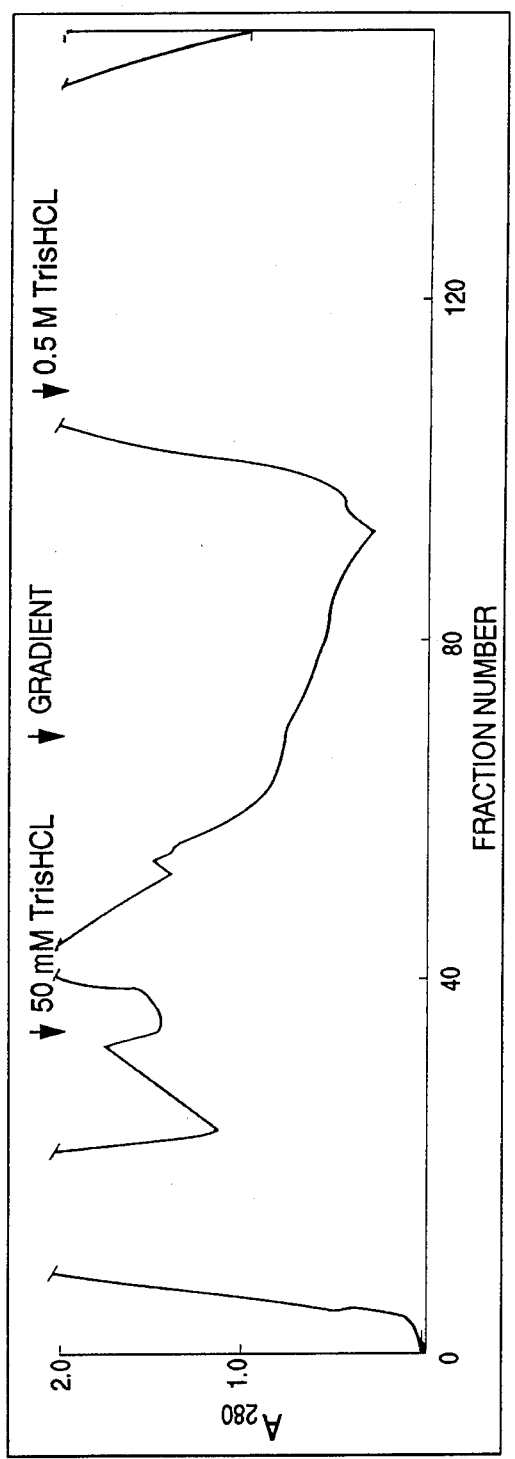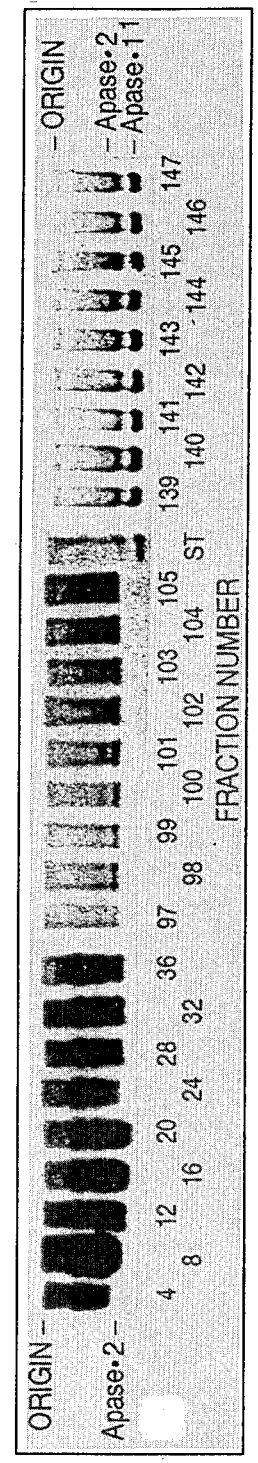
FIG.1A
FIG.1B

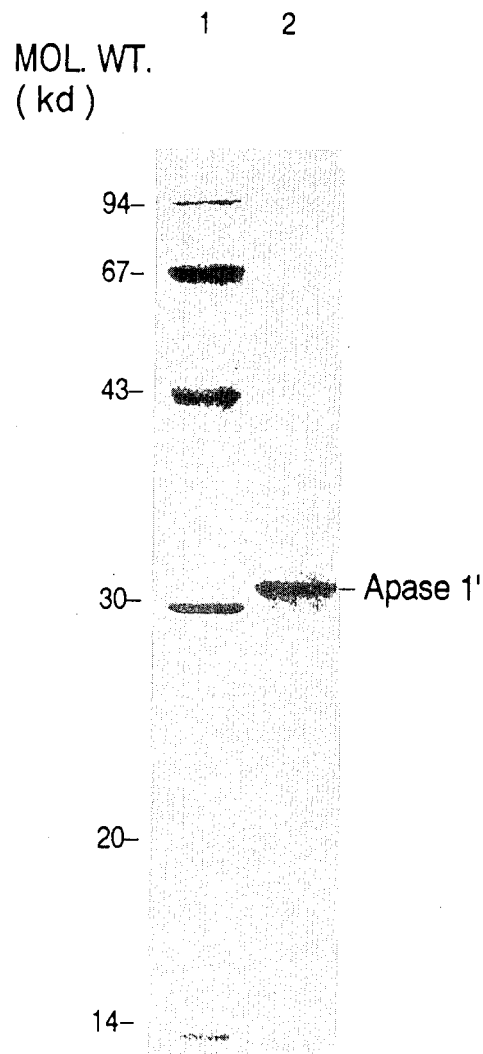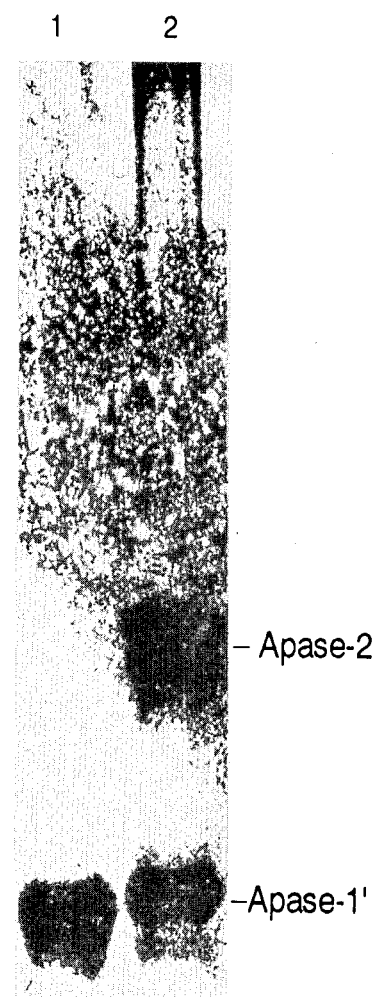
FIG. 3A.
FIG. 3B.

PURIFICATION OF APASE-1₁ AND RETRIEVAL OF THE NEMATODE RESISTANCE GENE

TECHNICAL FIELD

The invention relates to purification of enzymatic proteins and subsequent use of the purified protein in gene retrieval. In particular, it relates to purification of acid phosphatase-1 (Apase-1[1]) from tomato and use of the sequence derived from the purified protein to obtain an adjacent gene encoding nematode resistance.

BACKGROUND ART

The nematode resistance gene (Mi) of tomato is known to be closely linkded to the gene encoding acid phosphatase-1 (Apase-1[1]) on chromosome 6 (Rick, C.M., in *Genetic Maps* (1984) 3:474, Cold Spring Harbor Press). Apase-1[1] is a variant found in domesticated tomatoes presumably introduced when the gene encoding resistance to the nematode *Meliodogyne incognita* was transferred from the wild species *L. peruvianum* (Rick, C.M., et al, *Tomato Genetics Cooperative Reports* (1974) 24:25); and, indeed, Apase-1[1]is used as a selection marker in breeding nematode resistance (Medina-Filho, H.P., Ph.D. Thesis (1980) University of California, Davis).

Resistance to root knot nematodes is extremely important in a number of plants, including broadleaf crops such as tobacco, cotton, tomato, cucurbits, and other vegetables, fodder crops, and ornamentals. Nematode infestation results in a shallow and knotted root system leading to reduced feeder root development and reduced growth. Current methods of control, including treatment of soils with nematocides and crop management, are expensive and have undesirable environmental consequences in some instances. However, control of nematodes by providing resistance to the plant directly through the Mi gene is environmentally safe and, over the long run, inexpensive.

While the Mi gene is defined as a single locus and mapped on chromosome 6 of the tomato genome, the product of this gene is currently unknown. However, it is understood that transfer of this gene confers resistance to root-knotting nematodes, and that it resides close to a region encoding an acid phosphatase.

Acid phosphatases in general are present in a variety of forms and are characterized by their ability to hydrolyze phosphate monoesters at low pH. A number of these enzymes have been studied. Previous work with Apase-1[1] shows that it is inherited as a single locus, Aps1, close to the Mi locus (Forbes J. F., et al, *Tomato Genetics Cooperative Reports* (1976) 26:7–8).

DISCLOSURE OF THE INVENTION

The invention provides purified Apase-1[1], thus permitting the determination of the amino acid sequence and construction of appropriate oligonucleotide probes, and the production of polyclonal and monoclonal antibodies specific for this protein. The resulting probes and antibodies are useful to retrieve the gene encoding Apase-1[1], which can then be used, or portions thereof can then be used, to obtain the Mi gene encoding nematode resistance using chromosomal walking or jumping techniques.

Thus, in one aspect, the invention is directed to a method to purify tomato Apase-1[1] and to the product of this purification. In another aspect, the invention is directed to use of the purified protein for the preparation of anti-Apase-1[1] antibodies and to the antibodies so prepared. In still another aspect, the invention relates to oligomer probes constructed on the basis of the amino acid sequence of the purified enzymes, and to gene sequences retrieved using these probes. Equivalent gene sequences may also be retrieved from appropriate libraries using the above-mentioned antibodies. In still another aspect, the invention relates to genomic DNA fragments encoding Apase-1[1] or portions thereof which are retrieved using the Apase-1[1] gene or portions thereof, and specifically to the Mi genomic DNA obtained by techniques using the retrieved Apase-1[1] genomic sequences.

BRIEF DESCRIPTION OF THE DRAWINGS

FIG. 1 shows the elution profile from DEAE cellulose of an extract containing Apase-1[1].

FIG. 3 shows the results of polyacrylamide gel electrophoresis of purified Apase-1[1].

MODES OF CARRYING OUT THE INVENTION

Figure 2A:
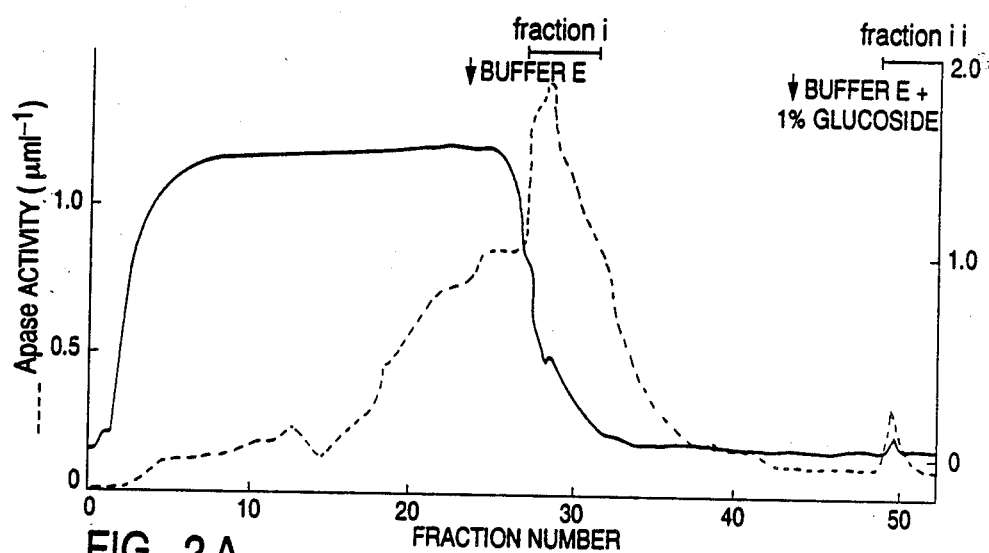
FIG. 2 shows an elution profile from ConA sepharose of Apase-1[1]-containing fractions.

As used herein, acid phosphatase-1 (or Apase-1, Apase-1[1]) refers to the protein encoded by the Aps1 gene locus immediately adjacent to the Mi region on chromosome 6, whose presence results in the nematode resistance in resistant tomato cultivars. The characteristics of the Apase-1[1] enzyme have been obtained through study of the protein obtained using the purification procedure described herein. Briefly, when subjected to nondenaturing PAGE, the Apase-1[1] shows a molecular weight of approximately 51 kd and is believed to be a dimer. When subjected to SDS-PAGE, the purified material shows an apparent molecular weight of 31 kd. The protein is considered to be a glycoprotein that has an amino acid composition as follows. Lys, 4.7 mole %; His, 3.1 mole %; Arg, 3.8 mole %; Cys, 0.9 mole %; Asx, 12.1 mole %; Thr, 5.4 mole %; Ser, 10.6 mole %; Glx, 12.0 mole %; Pro, 4.0 mole %; Gly, 9.6 mole %; Ala, 6.6 mole %; Val, 6.3 mole %; Met, 1.1 mole %; Ile, 4.3 mole %; Leu, 7.9 mole %; Tyr, 3.7 mole %; Phe, 4.0 mole %. The substrate specificity of the enzyme, measured by the release of phosphate from various substrates at 5 mM in citrate buffer, pH 4.6 at 30° C., given as a percentage of activity of the phosphatase with p-nitrophenylphosphate is as follows:

| Substrate | Apase-1[1] |
| --- | --- |
| α naphthylphosphate | 6 |
| β naphthylphosphate | 78 |
| glucose-1-phosphate | 0 |
| glucose-6-phosphate | 12 |
| ribose-5-phosphate | 54 |
| fructose-6-phosphate | 58 |
| 3-phosphoglyceric acid | 53 |
| glyceraldehyde-3-phosphate | 57 |
| 6-phosphoglucuronic acid | 57 |
| α glycerophosphate | 34 |
| β glycerophosphate | 10 |
| ATP | 0 |
| ADP | 2 |
| AMP | 4 |

It should be understood that deliberate or accidental mutations of the gene sequence referred to could occur, resulting in some alterations of the above-mentioned activities and amino acid compositions. Therefore, those characteristics are set forth herein as baseline parameters rather than as absolute requirements. It is, for example, well understood that other allelic variants of the Apase-1[1] gene, such as Apase-1+, are found in a variety of species. Allelic variants are specifically included in the definition. A protein falls within this definition if it is capable of purification using the methods described herein, and if encoded by a gene residing at the designated locus proximal to the Mi region.

The purified protein can be employed using generally recognized means to prepare antisera or monoclonal antibodies. For preparation of antisera, the purified protein is used to immunize a convenient mammalian subject, such as rats or mice, and the titers of antibodies formed in the serum monitored by immunoassays using the purified protein as antigen in standard ELISA or radioimmunoassay procedures. If monoclonal preparations are desired, antibody-producing cells are prepared from the immunized animal and immortalized, typically by fusion to a myeloma cell line, and the immortalized cells are screened in a similar manner for production of the desired antibodies.

The antibodies are useful in assay procedures for Apase-1 protein, and also in screening of properly constructed cDNA libraries for the presence of the gene encoding Apase-1. In this procedure, a cDNA library is constructed from the mRNA isolated from tomato cultivars harboring the Apase-1 gene using a phage vector, such as λgt11 (Young, R.A., et al. *Proc Natl Acad Sci U.S.A* (1983) 80:1194–1198). When this library is transformed into bacteria, recombinant Apase-1 is produced by those cells harboring the gene, and this production is monitored by assessment of the cultures for the presence of Apase-1 protein using standard immunoassay techniques with the antibody preparation.

The purified protein is also useful as a substrate for N-terminal sequencing, thus permitting sufficient amino acid sequence to be obtained to design oligomeric probes for alternative methods of screening appropriately constructed cDNA or genomic libraries. Amino acid sequencing techniques are now standard in the art, and a summary of such techniques may be found, for example, in the article by Allen, G., "Sequencing of Proteins and Peptides", in *Laboratory Techniques in Biochemistry and Molecular Biology* (1981), Work, T.S., et al, eds, Elsevier Science Publishers BV, Amsterdam, York, Oxford.

Once sufficient sequence is determined, probes are designed based on the genetic code. For use as probes, oligomers representing approximately six amino acid (17-18-mer) are useful in obtaining the desired sequences. Because of degenaracy in the codons for particular amino acids, sequences of this length are necessary to obtain the required number of matching nucleotides to retrieve desired sequences under stringent conditions; stringent conditions are required in order to eliminate false positives. Some of the sequence ambiguity due to degeneracy can be finessed by using inosine in place of degenerate nucleotides in the oligomer (Martin, F. H., et al, *Nucl Acids Res* (1985) 13:8927-8938).

In describing hybridization conditions, stringent conditions refer to conditions which permit base pairing only between highly homologus sequences. The stringency of the conditions is mainly controlled by formamide and salt concentration, and wash times and temperature, as in generally understood in the art (Maniatis, T., et al, *Molelcular Cloning* (1982), Cold Spring Harbor Press).

The oligomer probes are used to screen cDNA libraries prepared in a variety of protocols. In a typical preparation, mRNA is isolated from in vitro-cultured tomato cells or other tissue from tomato expressing Apase-1, using, for example, the procedure described by Hall, T.C., et al, *Proc Natl Acad Sci U.S.A* (1978) 75:3196. From the mRNA template, the cDNA library is constructed using the Okayama/Berg vector system (Okayama, H, et al, *Mol Cell Biol* (1983) 3:280–289) or a modification of this procedure, as described by Alexander, D.A., et al, *Gene* (1984) 31:79–89. The library may also be prepared in λgt11 or other phage vectors (supra). Isolated colonies are screened by hybridization and further characterized by DNA sequencing to confirm correspondence of the DNA to the previosuly determined required coding sequence for Apase-1.

The isolated Apase-1 cDNA can be used for the production of Apase-1 enzyme using standard recombinant methods, or, according to the method of the invention, can be used to retrieve the genomic DNA containing the Aps-1 locus from a genomic library derived from tomato chromosomes. For use in deriving the genomic DNA corresponding to the Aps-1 locus, a cDNA of at least about 20 nucleotides is required. Of course, the longer the cDNA sequence, the more easily the desired sequence can be retrieved. Preferable, therefore, to a 20 nucleotide sequence is a 50, or even better, a 500 nucleotide sequence. A full length clone is most desirable. By "corresponding to" the Aps-1 locus is meant sequences which are in the region of the gene responsible for the production of Apase-1.

The genomic library is prepared from tomato DNA partially digested with a restriction enzyme, by inserting the resulting fragments into cosmid or λ cloning vector (Maniatis, T., et al, *Molecular Cloning* (1982), Cold Spring Harbor Press). Cosmid vectors can accommodate about 50 kb of DNA; λ vectors, approximately 24 kb. These vectors are amplified in *E. coli* to obtain sufficient quantities of DNA. The genomic clone corresponding to at least a portion of the Aps-1 locus then provides end fragments which are used for chromosome walking. Thus, the fragment recognized as corresponding to the Aps-1 locus is cleaved with suitable restriction enzymes to obtain the appropriate end fragment. Using this end fragment, an overlapping genomic clone is isolated, and end fragments from this clone in turn used to obtain successive overlapping clones which are increasingly distant from the original starting position, and closer to the desired Mi gene. These techniques are well known in the art, and are outlined, for example, by Smith, C. L., et al, *Methods Enzymol* (in press). The basic walking procedure is also described by Steinmetz, M., et al, *Nature* (1982) 300:35-42.

More recently, "jumping" techniques, which permit larger distances to be bridged, have been disclosed. These techniques have been employed, for example, by Poustka, A., et al, *Trends Genet* (1986) 2:174-179; Poustka, A., et al, *Nature* (1987) 325:353-356; Collins, F. S., et al. *Proc Natl Acad Sci U.S.A.* (1984) 81:6812-6816. In this approach, the the genomic DNA library to be probed, consisting of extremely long, high molecular weight DNA of approximately several hundred kb, is prepared by lysis of cells embedded in blocks of low melting point agarose, followed by mild digestion with a chosen restriction enzyme. The long strands of DNA are then circularized, taking advantage of this restriction site, in the presence of a marker which is included in the circularized plasmid. The circularized DNA is then cleaved with a different restriction enzyme so as to delete the middle portion of the long-stranded DNA between the two ends. The now relatively short fragment, containing the two ends of the high molecular weight piece at either side of a linking marker sequence, form the jumping library from which the desired next overlapping fragment can be retrieved. In order to effect this, the double-ended fragments are probed with the original genomic DNA recognized as encoding the Apase-1[1] protein, and positive clones are used to probe the succeeding two-ended marker library. In this way, much larger stretches of the genome may be covered in short order, as in necessary in traversing the extremely long distances involved in mammalian chromosomes, as compared to bacterial or other more compactly constructed genomic DNA.

Verification that preparation of the Mi locus has been achieved is obtained by isolation of each overlapping genomic clone and testing it for the presence of the Mi nematode-resitance trail. In order to verify this trait, fragments from these clones are transferred into the Agrobacterium Ti vector system for transfer into plants (Simpson, R. B., et al, *Plant Mol Biol* (1986) 6:403–415). Roots from the transformed plants are screened for resistance to *M. incognita* using the in vitro assy of Huettel, R. N., et al, *Plant Nematology* (1985), pp 155 et seq, University of Massachusetts Agricultural Experiment Station).

Availability of the Mi genome permits the use of this DNA in transforming nematode-sensitive plants to nematode resitance. Both the genome itself and DNAs designed from it are useful in this regard.

EXAMPLES

EXAMPLE 1

Apase-1[1] Monitoring Assay

The presence of Apase-1[1] was assessed using cellulose acetate electrophoresis. The supernatants to be tested were loaded onto cellulose acetate paper and electrophoresis run for 15 min at 200 volts with 0.3M borate buffer, pH 7.8, using a Satorius electrophoresis apparatus. The paper was then stained at 30° C. until bands developed using 1 mg/ml black K salt; 0.75 mM $MgCl_2$, 50 mM sodium acetate, pH 4.6, plus 25 $\mu$l/ml of 1% $\beta$-naphthylphosphate (predissolved in 1:1 acetone water). The assay media were solidified with 12.5 mg/ml noble agar, according to the procedure modified from Vallejos, C. E., in *Plant Genetics and Breeding*, Part A (1983) Elsevier, Amsterdam, p. 498. Staining was from 15–45 min depending on the purity of the sample.

Apase activity was measured using the release of nitrophenol from p-nitrophenyl phosphate in 50 nM citrate buffer, pH 4.6, according to the method of Bergmeyer, H. U. in *Methods of Enzymatic Analysis* (1963) Academic Press, NY, pp 783–784. One unit of enzyme activity was defined 1 $\mu$M nitrophenol/min at 30° C. Protein concentration was determined by the method of Bradford (Bradford, M.M., *Anal Biochem* (1976) 72:248–254).

EXAMPLE 2

Purification of Apase-1[1] from Tomato

Cell suspension cultures of tomato (*Lycopersicon esculentum* Mill. cv VFNT) were maintained in 1 l flasks with 300 ml of a complete medium containing sucrose (DuPont, F. M., et al, *Plant Physiol* (1985) 77:64–68) with continuous shaking, at 27° C. and without lights. Two days before protein extraction, an additional 300 ml of medium minus phosphate was added For the purification, all steps were carried out below 10° C. Two kg of cells were filtered out of medium, homogenized in a Waring blender with 1.6 liters of Buffer A (0.1M Tris-HCl, pH 8.0, 5 mM dithioerythritol, 5 mM EDTA, 20%. polyvinylpolypyrollidone) and centrifuged at 6400 g for 10 min. The pellet was rehomogenized in a Waring blender with 0.5 l Buffer A and centrifuged.

From the combined supernatants a 55–85% saturated $(NH_4)_2SO_4$ precipitate was prepared by adding solid $(NH_4)_2SO_4$ and stirring for 30 The precipitate was recovered by centrifugation at 11,750 g for 30 min, redissolved to 300 ml in Buffer B (50 mM Tris-HCl, pH 7.4) and dialyzed overnight against 7 liters of Buffer B with one buffer change.

The desalted solution was loaded onto a 3×48 cm DEAE-cellulose column equilibrated with Buffer B and 7 ml fractions were collected. The column was washed with 250 ml Buffer B, then developed with 300 ml of a 50–500 mM Tris-HCl, pH 7.4, linear gradient, followed by a 500 mM Tris-HCl, pH 7.4, wash. The Apase-1[1] was tightly bound and eluted at 0.5M Tris, as shown in FIG. 1A, corresponding to fracrions 139–147. Fractions containing Apase-1[1] (140 ml), were determined by the cellulose acetate electrophoresis of Example 1, as shown in FIG. 1B, an also contained Apase-2. These fractions were dialyzed overnight against Buffer C (10 mM phosphate, pH 7.6).

The desalted, Apase-1[1]-containing fractions were loaded onto a 3×18 cm hydroxyapatite column equilibrated with Buffer C. Apase-1[1] was eluted by a 10–400 mM phophate linear concentration gradient (for large scale preparation this step was replaced by batch elution). Fractions containing Apase-1[1] (90 ml) were dialyzed overnight against Buffer D (25 mM Tris-HCl, 50 mM NaCl, pH 7.4).

The desalted fractions were loaded onto a 1×12 cm ConA sepharose column, equilibrated with Buffer D. Apase-1[1] was present mainly in the run-through. To obtain pure Apase-1[1] two additional passages of this material through the ConA sepharose column were required, as shown in FIG. 2. In the first recycled passage through ConA sepharose, as shown in FIG. 2A, after collection of the run-through, the column was washed with Buffer E (40 mM Tris-HCl, 200 mM NaCl, pH 7.4) followed by Buffer E plus 1% $\alpha$ methylglucoside. Fraction i, which was eluted with Buffer E, contained most of the Apase-1; fraction ii, eluted with buffer E plus 1% glucoside, contained Apase-2 plus some Apase-1.

The Apase-1 containing fractioni was dialyzed against 5 mM Tris-HCl, pH 7.4, lyophylized, redissolved in 4 ml water, and reloaded onto the ConA column. Apase-1, eluted with Buffer E, pH 8.5 (fraction iii) as shown in FIG. 2B, was homogeneous.

Figure 2B:
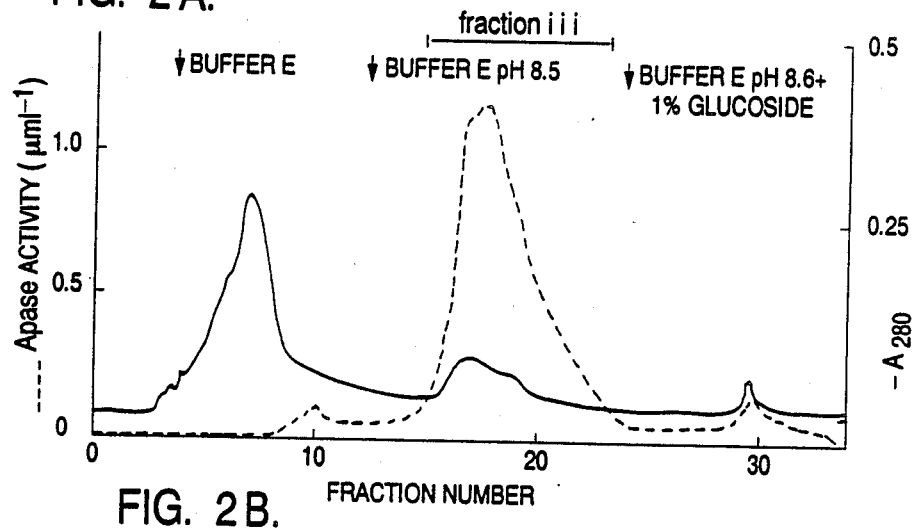

The purified Apase-1[1] protein was recovered from the peak shown in FIG. 2B and verified to be homogeneous by gel chromatography. FIG. 3 shows these results. Panel A shows SDS PAGE, size standards in line 1 and the recovered fraction iii in lane 2. Panel B shows non-denaturing PAGE stained for Apase activity; fraction iii in lane 1 and a mixture of Apase-1 and Apase-2 in lane 2. Both types of PAGE show fraction iii to be a single band corresponding to Apase-1.

The purified protein is then used for antibody production and for amino acid sequencing for design of appropriate oligomeric probes.

We claim:

1. A method to purify Apase-1¹ which process comprises
    (a) subjecting a crude extract from tomato cells to ammonium sulfate precipitation at 55–85% saturation;
    (b) desalting the precipitate;
    (c) subjecting the desalted preparation of (b) to anion exchange chromatography and collecting fractions contaning Apase-1¹;
    (d) desalting the fractions;
    (e) subjecting the desalted preparation of (d) to chromatography on hydroxyapatite and collecting fractions containing Apase-1¹;
    (f) desalting the fractions obtained in (e);
    (g) subjecting the desalted preparation of (f) to affinity chromatography and recovering the Apase-1¹ fractions.

2. The method of claim 1 wherein the anion exchange chromatography employs DEAE cellulose.

3. The method of claim 1 wherein the affinity chromatography employs ConA sepharose.

4. A method to purify Apase-1¹ from tomato which comprises
    (a) extracting cultured tomato cells in approximately pH 8 buffer;
    (b) precipitating the Apase-1¹ protein from the extract using 55–85% ammonium sulfate;
    (c) redissolving the precipitate and desalting;
    (d) subjecting the desalted solution to chromatography on DEAE cellulose and eluting the Apase-1¹ fractions using a Tris-HCl pH 7.4 gradient to 500 mM HCl;
    (e) desalting the Apase-1¹-containing fraction of (d);
    (f) subjecting the Apase-1¹-containing fractions to hydroxyapatite column chromatography, eluting with a phosphate linear concentration gradient to 400 mM phosphate;
    (g) desalting the Apase-1¹-containing fractions of (f);
    (h) subjecting the desalted Apase-1¹ fractions of (g) to chromatography on ConA sepharose and eluting the Apase-1¹ fractions with 40 mM Tris, 200 mM NaCl, pH 7.4.

5. Apase-1¹ prepared by the method of claim 1.

6. A purified Apase-1¹ protein having an apparent molecular weight on SDS-PAGE of 31 kd and an amino acid composition consisting of: Lys, 4.7 mole %; His, 3.1 mole %; Arg, 3.8 mole %; Cys, 0.9 mole %; Asx, 12.1 mole %; Thr, 5.4 mole %; Ser, 10.6 mole %; Glx, 12.0 mole %; Pro, 4.0 mole %; Gly, 9.6 mole %; Ala, 6.6 mole %; Val, 6.3 mole %; Met, 1.1 mole %; Ile, 4.3 mole %; Leu, 7.9 mole %; Tyr, 3.7 mole %; Phe, 4.0 mole %.

* * * * *